US008190453B2

(12) United States Patent
Rowe, III et al.

(10) Patent No.: US 8,190,453 B2
(45) Date of Patent: May 29, 2012

(54) SYSTEMS AND METHODS FOR VERIFYING AND EDITING ELECTRONICALLY TRANSMITTED CLAIM CONTENT

(75) Inventors: James Couser Rowe, III, Sugar Hill, GA (US); Roger G. Pinsonneault, Alpharetta, GA (US)

(73) Assignee: NDCHealth Corporation, Atlanta, GA (US)

( * ) Notice: Subject to any disclaimer, the term of this patent is extended or adjusted under 35 U.S.C. 154(b) by 619 days.

(21) Appl. No.: 10/439,422

(22) Filed: May 16, 2003

(65) Prior Publication Data

US 2004/0078247 A1    Apr. 22, 2004

Related U.S. Application Data

(60) Provisional application No. 60/381,395, filed on May 16, 2002.

(51) Int. Cl.
G06Q 40/00 (2012.01)
G06Q 50/00 (2012.01)

(52) U.S. Cl. ............................... 705/4; 705/2

(58) Field of Classification Search .................. 705/1, 36, 705/38, 40, 26, 14, 51, 42, 44, 2–4; 715/531, 715/530; 707/102, 100, 104.1, 10
See application file for complete search history.

(56) References Cited

U.S. PATENT DOCUMENTS

| 5,235,702 A | * | 8/1993 | Miller | 707/102 |
| 5,359,509 A | * | 10/1994 | Little et al. | 705/2 |
| 5,544,044 A | * | 8/1996 | Leatherman | 705/3 |
| 5,550,734 A | * | 8/1996 | Tarter et al. | 705/2 |
| 5,628,530 A | | 5/1997 | Thornton | |
| 5,644,778 A | * | 7/1997 | Burks et al. | 705/2 |
| 5,704,044 A | * | 12/1997 | Tarter et al. | 705/4 |
| 5,832,447 A | * | 11/1998 | Rieker et al. | 705/2 |
| 5,950,169 A | * | 9/1999 | Borghesi et al. | 705/4 |
| 6,006,242 A | * | 12/1999 | Poole et al. | 715/531 |
| 6,012,035 A | | 1/2000 | Freeman et al. | |
| 6,073,104 A | * | 6/2000 | Field | 705/1 |

(Continued)

FOREIGN PATENT DOCUMENTS

CA    2482370 A1    3/2006

(Continued)

OTHER PUBLICATIONS

Glaser, Martha. Computer eliminates third-party administrator. Drug Topics. Oradell: May 3, 1993.vol. 137, Iss. 9; p. 54, 3 pgs. [Retrieved from Internet Apr. 11, 2007]. URL: <http://proquest.umi.com/pqdweb?did=779533&sid=5&Fmt=3&clientId=19649&RQT=309& VName=PQD>.*

(Continued)

Primary Examiner — Gerald J. O'Connor
Assistant Examiner — Natalie A Pass
(74) Attorney, Agent, or Firm — Sutherland Asbill & Brennan LLP

(57) ABSTRACT

Systems and methods verify the content of an electronically transmitted claim, such as a healthcare claim by intercepting the claim, reviewing the claim's contents, and comparing the claim to pre-established claim criteria established by a payer or both a healthcare service provider and payer. If the claim contains the appropriate content the claim is forwarded to its intended recipient, typically a payer such as an insurance company or government healthcare payer; otherwise the claim may be returned to the sender, e.g., a pharmacy, with an indication that it does not contain the correct content. Additionally, the claim may be edited by the system and forwarded in correct form to its intended recipient.

20 Claims, 4 Drawing Sheets

U.S. PATENT DOCUMENTS

| | | | |
|---|---|---|---|
| 6,208,973 B1* | 3/2001 | Boyer et al. | 705/2 |
| 6,324,516 B1* | 11/2001 | Shults et al. | 705/2 |
| 6,341,265 B1* | 1/2002 | Provost et al. | 705/2 |
| 6,343,271 B1* | 1/2002 | Peterson et al. | 705/4 |
| 6,632,251 B1* | 10/2003 | Rutten et al. | 715/530 |
| 6,671,692 B1* | 12/2003 | Marpe et al. | 707/102 |
| 6,671,693 B1* | 12/2003 | Marpe et al. | 707/102 |
| 6,757,898 B1 | 6/2004 | Ilsen et al. | |
| 6,769,228 B1 | 8/2004 | Mahar | |
| 7,155,397 B2 | 12/2006 | Alexander et al. | |
| 2001/0037224 A1* | 11/2001 | Eldridge et al. | 705/4 |
| 2001/0041993 A1* | 11/2001 | Campbell | 705/4 |
| 2002/0002495 A1 | 1/2002 | Ullman | |
| 2002/0035488 A1* | 3/2002 | Aquila et al. | 705/4 |
| 2002/0049617 A1* | 4/2002 | Lencki et al. | 705/4 |
| 2002/0055856 A1* | 5/2002 | Adams | 705/2 |
| 2002/0065687 A1* | 5/2002 | Onoue | 705/4 |
| 2002/0087583 A1 | 7/2002 | Morgan et al. | |
| 2002/0111832 A1 | 8/2002 | Judge | |
| 2002/0133503 A1* | 9/2002 | Amar et al. | 707/104.1 |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0083903 A1* | 5/2003 | Myers | 705/2 |
| 2003/0120588 A1* | 6/2003 | Dodd et al. | 705/38 |
| 2003/0149594 A1* | 8/2003 | Beazley et al. | 705/2 |
| 2003/0149625 A1 | 8/2003 | Leonardi et al. | |
| 2003/0154163 A1 | 8/2003 | Phillips et al. | |
| 2003/0191665 A1* | 10/2003 | Fitzgerald et al. | 705/2 |
| 2003/0229540 A1 | 12/2003 | Algiene | |
| 2004/0039599 A1 | 2/2004 | Fralic | |
| 2004/0073457 A1 | 4/2004 | Kalies | |
| 2004/0078234 A1 | 4/2004 | Tallal, Jr. | |
| 2004/0093242 A1* | 5/2004 | Cadigan et al. | 705/4 |
| 2004/0117323 A1 | 6/2004 | Mindala | |
| 2004/0148198 A1 | 7/2004 | Kalies | |
| 2004/0249745 A1 | 12/2004 | Baaren | |
| 2005/0015280 A1 | 1/2005 | Gabel et al. | |
| 2005/0060201 A1 | 3/2005 | Connely, III et al. | |
| 2005/0102169 A1 | 5/2005 | Wilson | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240473 A1 | 10/2005 | Ayers, Jr. et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0149784 A1 | 7/2006 | Tholl et al. | |
| 2006/0184391 A1 | 8/2006 | Barre et al. | |
| 2006/0259363 A1 | 11/2006 | Jhetam | |
| 2007/0005402 A1 | 1/2007 | Kennedy et al. | |
| 2007/0050209 A1 | 3/2007 | Yered | |
| 2007/0136100 A1 | 6/2007 | Daugherty et al. | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |

FOREIGN PATENT DOCUMENTS

| | | |
|---|---|---|
| WO | WO 9503569 A3 | 2/1995 |
| WO | WO 0039737 A1 | 7/2000 |
| WO | WO 2007025295 A2 | 3/2007 |

OTHER PUBLICATIONS

McKesson & American Pharmacy Alliance Agree to Offer Omnilink Connectivity to Retail Pharmacies; More Than 11,000 Pharmacies Gain Ability to Access Centralized Pharmacy Application. Bus.Wire. New York: Jul. 28, 1998. p. 1. [Retr. Internet Oct. 30, 2007] URL: <http://proquest.umi.com/pqdweb?did=32392868&sid=4& Fmt=3& clientId=19649&RQT=309&VName=PQD>.*

NDC Health Information Services Announces Contract With Arrow Pharmacy and Nutrition Centers for Pre & Post Editing Service. PR Newswire. New York: Mar. 11, 1999. p. 1. [Retr. from Internet Oct. 30, 2007] URL: <http://proquest.umi.com/pqdweb?did=39644468& sid=3&Fmt=3&clientId=19649&RQT=309&VName=PQD>.*

National Data Announces Contracts With Six Pharmacies Spanning the U.S for Pre & Post Editing Service. PR Newswire. New York: Mar. 15, 1999. p. 1. [Retr. from Internet Apr. 11, 2007] URL: <http://proquest.umi.com/pqdweb?did=39727242&sid=3&Fmt=3& clientId=19649&RQT=309&VName=PQD>.*

NDC Health Provides United Drugs With Intelligent Value-Added Network Services and New Information Solutions. PR Newswire. New York: Dec. 12, 2000. p. 1. [Retr. from Internet Apr. 11, 2007] URL: <http://proquest.umi.com/pqdweb?did=65133864&sid=4& Fmt=3&clientId=19649&RQT=309&VName=PQD>.*

Pharmacy Industry Leaders Launch Firm to Supply Real-Time Data. PR Newswire. New York: Jul. 30, 2001. p. 1. [Retr. from Internet Oct. 30, 2007] URL: <http://proquest.umi.com/pqdweb?did=77135077& sid=11&Fmt=3&clientId=19649&RQT=309&VName=PQD>.*

Wholesalers Get Into Technology Game. Chain Drug Review. Feb. 15, 1999. p. RX20. [Retr. from Internet Oct. 30, 2007] URL: <http://www.accessmylibrary.com/coms2/summary_0286-487914_ITM>.*

Oct. 2, 2006 letter from Whitaker, Chalk, Swindle & Sawyer, LLC to Sutherland, Asbill & Brennan, LLP with enclosures of press release copies related to eRx Network, LLC.

Letter addressed to Scott Mackenzie of Per-Se Technologies from Mack Ed Swindle, Esq. of Whitaker, Chalk, Swindle & Sawyer, L.L.P. dated Jul. 21, 2006, regarding U.S. Appl. No. 10/133,001 and U.S. Appl. No. 10/439,422 (2 pages).

Letter addressed to Mac Ed Swindle, Esq. of Whitaker, Chalk, Swindle & Sawyer, L.L.P. from Griff Griffin, Esq. of Sutherland, Asbill & Brennan LLP dated Sep. 14, 2006, regarding U.S. Appl. No. 10/133,001 (2 pages).

Letter addressed to Griff Griffin, Esq. of Sutherland Asbill & Brennan LLP from Mack Ed Swindle, Esq. of Whitaker, Chalk, Swindle & Sawyer, L.L.P. dated Oct. 2, 2006 (2 pages); and attached press releases dated 2001 and 2002 (2 pages), regarding U.S. Appl. No. 10/133,001 and U.S. Appl. No. 10/439,422.

Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007 (1 page);and attached Affidavit of Ben Loy (10 pages), regarding U.S. Appl. No. 10/133,001.

Exhibit A ("Public-Key Cryptography, NIST Special Publication 800-2," Apr. 1991) to Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (132 pages).

Exhibit B ("Escrowed Encryption Standard (EES)," Feb. 9, 1994) to Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (8 pages).

Exhibit C ("Entity Authentication Using Public Key Cryptography," Feb. 18, 1997) to Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (50 pages).

Exhibit D ("Internet x. 509 Public Key Infrastructure Certificate Management Protocols," Mar. 1999) to Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (65 pages).

Exhibit E ("PDX 4.0 Pharmacy Manual, Canada Claims section from Jan. 2000") to Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (4 pages).

Letter addressed to Mack Ed Swindle, Esq. of Whitaker, Chalk, Swindle & Sawyer, L.L.P. from Christopher J. Chan, Esq. of Sutherland, Asbill & Brennan LLP dated May 30, 2007, regarding U.S. Appl. No. 10/133,001 (2 pages).

Letter addressed to Mr. Kevin King of Sutherland Asbill & Brennan LLP and Mr. Paul J. Quinar of Per Se Technologies from Mack Ed Swindle, Esq. of Whitaker, Chalk Swindle & Sawyer, L.L.P. dated Feb. 12, 2007, regarding U.S. Appl. No. 11/364,987 (2 pages).

Letter addressed to Mack Ed Swindle, Esq. of Whitaker, Chalk, Swindle & Sawyer, L.L.P. from Christopher J. Chan, Esq. of Sutherland, Asbill & Brennan LLP dated Mar. 14, 2007, regarding U.S. Appl. No. 11/364,987 (2 pages).

Letter addressed to Christopher J. Chan, Esq. of Sutherland Asbill & Brennan LLP from Mack Ed Swindle, Esq. of Whitaker, Chalk, Swindle & Sawyer, L.L.P. dated May 15, 2007, regarding U.S. Appl. No. 11/364,987 (3 pages) and referenced attachments (OPUS-ISM LLC web page—1 page) and (CareMax Connection brochure excerpt—2 pages).

Letter addressed to Mack Ed Swindle, Esq. of Whitaker, Chalk, Swindle & Sawyer, L.L.P. from Christopher J. Chan, Esq. of Sutherland, Asbill & Brennan LLP dated Jun. 7, 2007, regarding U.S. Appl. No. 11/364,987 (2 pages).

Letter addressed to Mack Ed Swindle, Esq. of Whitaker, Chalk, Swindle & Sawyer, L.L.P. from Griff Griffin, Esq. of Sutherland Asbill & Brennan LLP dated Sep. 14, 2006 regarding U.S. Appl. No. 10/439,422 (2 pages).

Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/439,422 (1 page).

Affidavit of Ken Hill to letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/439,422 (5 pages) and attached Exhibits A (5 pages) and B (49 pages).

Letter addressed to Mack Ed Swindle, Esq. of Whitaker, Chalk, Swindle & Sawyer, L.L.P. from Christopher J. Chan, Esq. of Sutherland, Asbill & Brennan LLP dated Jun. 7, 2007, regarding U.S. Appl. No. 10/439,422 (2 pages).

International Preliminary Report issued on Apr. 7, 2009 for International Patent Application No. PCT/US2003/015992.

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions. Britain's Traditionally Cautious National Health Service is Starting Trials for Online Prescription, with the Aim of Cutting Costs, Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132, vol. 63, Issue 1, USA.

Anonymous, TechRx Announces Successful Beta Deployment of T-Rex. PR Newswire. May 13, 2002.

* cited by examiner

SYSTEMS AND METHODS FOR VERIFYING AND EDITING ELECTRONICALLY TRANSMITTED CLAIM CONTENT

RELATED APPLICATION DATA

The present application claims the benefit of U.S. Provisional Patent Application Ser. No. 60/381,395, filed May 16, 2002, titled "Systems and Methods for Verifying Electronically Transmitted claim Content", which is hereby incorporated by reference as if set forth fully herein.

FIELD OF THE INVENTION

The present invention relates generally to claim processing systems, and more particularly, to claim processing systems for verifying and editing claims electronically transmitted from healthcare service providers to payers, such as insurance companies.

BACKGROUND OF THE INVENTION

In recent years medical and prescription claim processing has become a highly automated process. Today, thousands of claims are electronically transmitted daily from healthcare service providers ("providers") to insurance companies and other payers (collectively, "payers"). These claims are processed and stored in near-real time, thereby expediting the process of paying healthcare service providers for their services.

Unfortunately, however, many electronically-transmitted claims are rejected by payers because the claims' contents are in error. In fact, payers typically reject almost 20 percent of electronically transmitted claims because of errors in the claims. Claim errors include insufficient information, improper information, and/or conflicting information. This problem is particularly challenging due to the wide variety of payers and medical and pharmaceutical plans, each of which often has its own standards dictating the content of an electronically-transmitted claim.

At a minimum, reducing the number of claim rejections would reduce costs associated with claim communication and processing. Additionally, reducing the number of claim rejections will increase the speed at which claims are processed because claims will not need to be submitted multiple times to correct errors. Therefore, what is needed is an automated system and method for automatically reviewing the contents of a claim transmitted to a payer, and for identifying problems with the claim before it is transmitted to the payer. Preferably, such a system and method would also automatically edit the claim such that it complies with payer requirements.

SUMMARY OF THE INVENTION

The present invention verifies the content of an electronically transmitted claim, such as a healthcare claim (e.g., a pharmaceutical claim or a medical claim) by intercepting the claim, reviewing the claim's contents, and comparing the claim to pre-established claim criteria established by a payer or both the healthcare provider and payer. If the claim contains the appropriate content the claim is forwarded to its intended recipient; otherwise the claim may be returned to the sender, e.g., a pharmacy, with an indication that it does not contain the correct content. Alternatively, the claim may be altered by the system and forwarded in correct form to its intended recipient, typically a payer such as an insurance company or government healthcare payer.

The system of the present invention includes a pharmacy POS system, a host server, and a payer. The host server is in electrical communication with the provider and payer to transmit claims and claim-related communications (e.g., confirmations, acceptances, rejections, etc.) between the provider and payer. The system also includes a claim editing module, which may also be incorporated within the host server. The claim editing module receives pre-established claim criteria established by a payer or by a payer and provider, which the claim editing module stores in a database. The claim editing module can store such information for a plurality of payers. The claim editing module receives a claim intended for a particular payer, and compares the claim's contents with the pre-established criteria for the particular payer (and optionally, with pre-established criteria for the provider, e.g., pharmacy, transmitting the claim). The claim editing module is operable to identify those claims that do not meet particular criteria such that the claims are unacceptable to the payer. Unacceptable claims can comprise claims lacking one or more required fields, claims having too many fields, or claims having data outside pre-established limits defined by the payer, a third party or the claim processing service.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention is described below with reference to block diagrams and flowchart illustrations of systems, methods, apparatuses and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Figure 1:
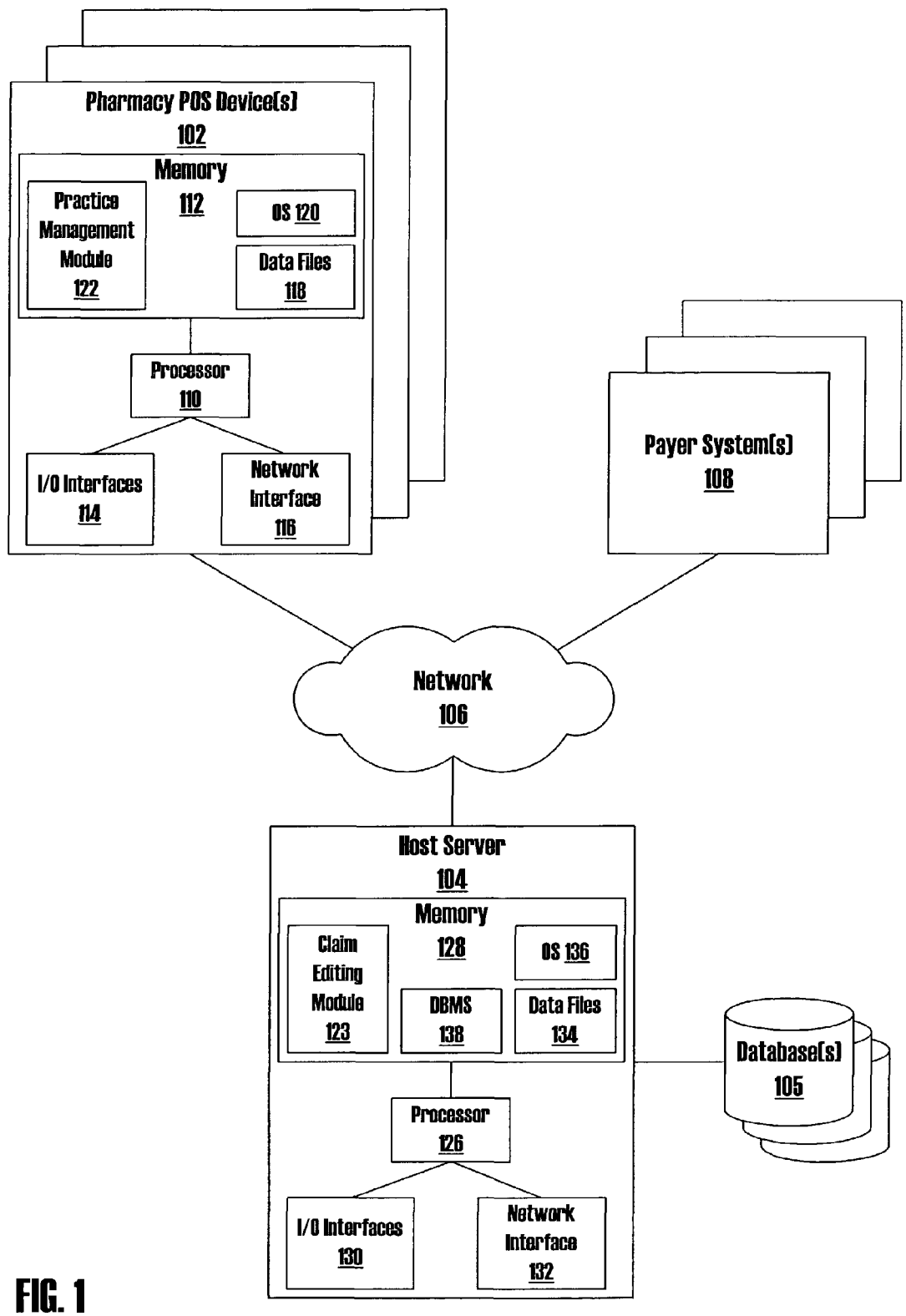
FIG. 1 shows a claim processing system according to one aspect of the present invention.

Exemplary embodiments of the present invention will hereinafter be described with reference to the figures, in which like numerals indicate like elements throughout the several drawings. FIG. 1 shows a block diagram claim processing system according to one aspect of the present invention. In particular, FIG. 1 is an exemplary operating environment for implementation of certain embodiments of the present invention, including a pharmacy point-of-service ("POS") device 102, a host server 104 and a payer system 108, which are each configured for accessing and reading associated computer-readable media having stored thereon data and/or computer-executable instructions for implementing the various methods of the present invention. Generally, network devices and systems include hardware and/or software for transmitting and receiving data and/or computer-executable instructions over a communications link and a memory for storing data and/or computer-executable instructions. Network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

As shown in FIG. 1, a pharmacy POS device 102 may be in communication with the host server 104 via a network 106. The pharmacy POS device 102 may be configured for receiving prescription claim data, creating prescription transactions therefrom and transmitting said prescription transactions to the host server 104. Prescription claim data includes any data that is typically provided by a patient, pharmacist and/or other health care provider in relation to filling a prescription and/or requesting approval or authorization for payment from a payer or claim adjudicator. A payer may be an insurance company, a financial institution or another financial service provider. Prescription claim data may be input to the pharmacy POS device 102 by a pharmacist or other health care provider or may be received by the pharmacy POS device 102 in electronic form from an electronic prescription service (not shown). The pharmacy POS device 102 may be configured for handling other types of prescription transactions.

Prescription claim transactions are electronic records or messages intended to facilitate the communication of prescription information. For example, prescription claim transactions are intended to communicate prescription claim data between pharmacies (i.e., providers) and payers. Although prescription claim transactions will be discussed hereinafter, it should be understood that the various systems and method of the invention may be practiced in connection with other types of prescription transactions or independently of prescription transactions (e.g., raw prescription data). The content and format of a prescription claim may vary depending on which standard or protocol is used. In general, however, prescription claim transactions will identify at least the intended payer recipient, the drug product to be dispensed, e.g., by National Drug Code number ("NDC#"), the quantity to be dispensed and the days supply, whether the prescription claim relates to a new prescription or a refill prescription, and billing-related information.

Prescription claim transactions may be transmitted from the pharmacy POS device 102 to the host server 104 in batch, real-time or near real-time. Pharmacy POS devices can connect to the host server 104 through a variety of methods, including dial-up, frame relay or leased-line. The entire system is preferably supported by redundant software, communications links, and uninterruptible power supplies, thereby ensuring that all connections will provide reliable, continuous operation. The system also preferably ensures that all of provider-submitted claims transactions are routed quickly, accurately, and consistently. The claim processing system eliminates provider postage and handling expenses by allowing pharmacies (or other healthcare entities) to submit claims to payer systems 108 electronically, thereby substantially reducing the costs of submitting claims and speeding up providers' payment cycles.

In certain embodiments, the host server 104 may serve as a clearinghouse for multiple payer systems 108. As noted above, payer systems 108 may include systems operated by insurance companies, financial institutions and other financial service providers. In its capacity as a clearinghouse, the host server 104 is operable to parse prescription claim transactions and forward them to the appropriate payer system 108 for processing. Approval, authorization or rejection messages may be returned to the host server 104 from the payer systems 108 and such messages may be forwarded by the host server 104 to the pharmacy POS device 102.

In serving as a clearinghouse, the host server 104 may also be configured for performing pre-processing and post-processing of prescription claim transactions. Pre-processing and post-processing refers to real-time or near real-time validation and management of prescription claim data in order to maximize prescription claim reimbursement and minimize claim submission errors. Pre-processing and post-processing may generate messaging alerts and/or retrospective reports supporting "usual and customary" price comparisons, average wholesale price ("AWP") edits, dispense as written ("DAW") brand appropriateness, and numerous other screening processes for facilitating rapid and accurate validation of prescription claims.

In accordance with the present invention, the host server 104, and more particularly, the claim editing module 123, may be configured for performing certain claim screening and editing processes for the detection and correction of claim errors in a prescription transaction. Therefore, the claim editing module 123 may comprise computer-executable instructions for performing various screening processes for reviewing and editing pharmacy claims and for managing related messaging and reporting functions. The host server 104 intercepts claims transmitted from the pharmacy POS device 102, and the claim editing module 123 parses and examines the claim's contents. The claim editing module 123 then compares the claim to pre-established claim criteria established by a third party, typically, a payer. If the claim contains the appropriate content the claim editing module 123 forwards the claim to its intended payer; otherwise the claim may be returned to the sender with an indication that it does not contain the correct content. For instance, where a claim fails to meet payer-provided claim criteria, the claim editing module 123 can transmit a claim reject message to the pharmacy POS device 102, so that the pharmacy can correct the claim error and retransmit the claim. Reject messages may indicate that a prescription claim has been rejected, provide a pharmacist with information about the claim error, and may encourage the pharmacist to correct the prescription claim.

The claim criteria can also dictate actions that should be taken, such as messages transmitted to a pharmacy concerning the prescription. The claim criteria can also instruct the module 123 that the claim should be compared against databases of objective information, such as drug lists or physician DEA numbers, or against historical data, such as historical consumer claim information, stored in one or more databases associated with the host server 104 and described below. The claim may also be altered by the claim editing module 123 and forwarded in correct form to the intended payer system 108. Finally, the claim screening and editing processes according to the present invention are also designed to capture certain prescription claim data for subsequent analysis and reporting related to claim errors transmitted from pharmacy POS devices 102.

Referring again to FIG. 1, it will be appreciated that the pharmacy POS device 102 may be any processor-driven device, such as a personal computer, laptop computer, handheld computer and the like. In addition to a processor 110, the pharmacy POS device 102 may further include a memory 112, input/output ("I/O") interface(s) 114 and a network interface 116. The memory 112 may store data files 118 and various program modules, such as an operating system ("OS") 120 and a practice management module 122. The practice management module 122 may comprise computer-executable instructions for performing various routines, such as those for creating and submitting prescription claim transactions. I/O interface(s) 114 facilitate communication between the processor 110 and various I/O devices, such as a keyboard, mouse, printer, microphone, speaker, monitor, etc. The network interface 116 may take any of a number of forms, such as a network interface card, a modem, etc. These and other components of the pharmacy POS device 102 will be apparent to those of ordinary skill in the art and are therefore not discussed in more detail herein.

Similarly, the host server 104 may be any processor-driven device that is configured for receiving and fulfilling requests related to prescription claim transactions. The host server 104 may therefore include a processor 126, a memory 128, input/output ("I/O") interface(s) 130 and a network interface 132. The memory 128 may store data files 134 and various program modules, such as an operating system ("OS") 136, a database management system ("DBMS") 138 and the claim editing module 123. The host server 104 may include additional program modules (not shown) for performing other pre-processing or post-processing methods and for providing clearinghouse services. Those skilled in the art will appreciate that the host server 104 may include alternate and/or additional components, hardware or software. In addition, the host server 104 may be connected to a local or wide area network (not shown) that includes other devices, such as routers, firewalls, gateways, etc.

The host server 104 may include or be in communication with one or more database 105. The database 105 may store, for example, data relating to pharmacies, payers, state prescription laws, prescription drugs, formularies, and consumers, such as typical doses filled by consumers, typical drugs prescribed by doctors, most common daily dose values, common daily dose values, likelihood indicators and other data used in the various claim screening and editing processes described herein after. The database 105 may also store reports and other data relating to the results of the claim screening and edit processes. The database 105 may of course also store any other data used or generated by the host server 104 or claim editing module 123, such as data used in other pre-processing and post-processing methods and reports generated thereby. Although a single database 105 is referred to herein for simplicity, those skilled in the art will appreciate that multiple physical and/or logical databases may be used to store the above mentioned data. For security, the host server 104 may have a dedicated connection to the database 105, as shown. However, the host server 104 may also communicate with the database 105 via a network 106.

The network 106 may comprise any telecommunication and/or data network, whether public or private, such as a local area network, a wide area network, an intranet, an internet and/or any combination thereof and may be wired and/or wireless. Due to network connectivity, various methodologies as described herein may be practiced in the context of distributed computing environments. Although the exemplary pharmacy POS device 102 is shown for simplicity as being in communication with the host server 104 via one intervening network 106, it is to be understood that any other network configuration is possible. For example, the pharmacy POS device 102 may be connected to a pharmacy's local or wide area network, which may include other devices, such as gateways and routers, for interfacing with another public or private network 106. Instead of or in addition to a network 106, dedicated communication links may be used to connect the various devices of the present invention.

Those skilled in the art will appreciate that the operating environment shown in and described with respect to FIG. 1 is provided by way of example only. Numerous other operating environments, system architectures and device configurations are possible. For example, the invention may in certain embodiments be implemented in a non-networked environment, in which a stand-alone pharmacy POS device 102 executes one or more claim editing module(s) 123. Accordingly, the present invention should not be construed as being limited to any particular operating environment, system architecture or device configuration.

Using the claim processing system described above, providers can transmit in real-time provider-submitted claims to an appropriate payer and return a claim approval or rejection within seconds. Thus, the claim processing system of the present invention can streamline provider claim processing operations and increase productivity for both providers and benefit plans. To enable the provider to input claims for electronic transmission to the claim processing system and payer, the pharmacy POS device 102 may comprise software that receives claim data entered by a user through a graphical user interface (GUI). According to one aspect of the invention, no claim processing software resides on the POS device 102, other than an Internet browser, because the GUI and one or more interfaces for inputting claim data are stored by the claim processing system and remotely accessible by the POS device 102 via an Internet connection, satellite or cellular network, LAN, WAN, or the like.

Using the GUI information such as a patient's name, birth date, address, telephone number and other identifying information is entered with claim-specific information, such as drug prescription or medical service or procedure. The identity of the pharmacy is also included in the claim data along with additional information known to those of ordinary skill in the art.

According to one aspect of the invention the claim data fields are defined by a particular payer such that the POS device 102 should provide only the claim data requested by the payer to which the claim is transmitted. According to another aspect of the invention the claim data is defined by a pre-established standard or transaction format well known to those of skill in the art. Once the claim is entered, it is transmitted to the host server 104 via any of the methods described above. The claim is then processed by the host server 104 and forwarded to the appropriate payer system 108. Preferably, the claim processing system, and more particularly, the host server 104, is an all-payer solution allowing providers to use a single application to connect to key government and commercial payers across the country.

Figure 2:
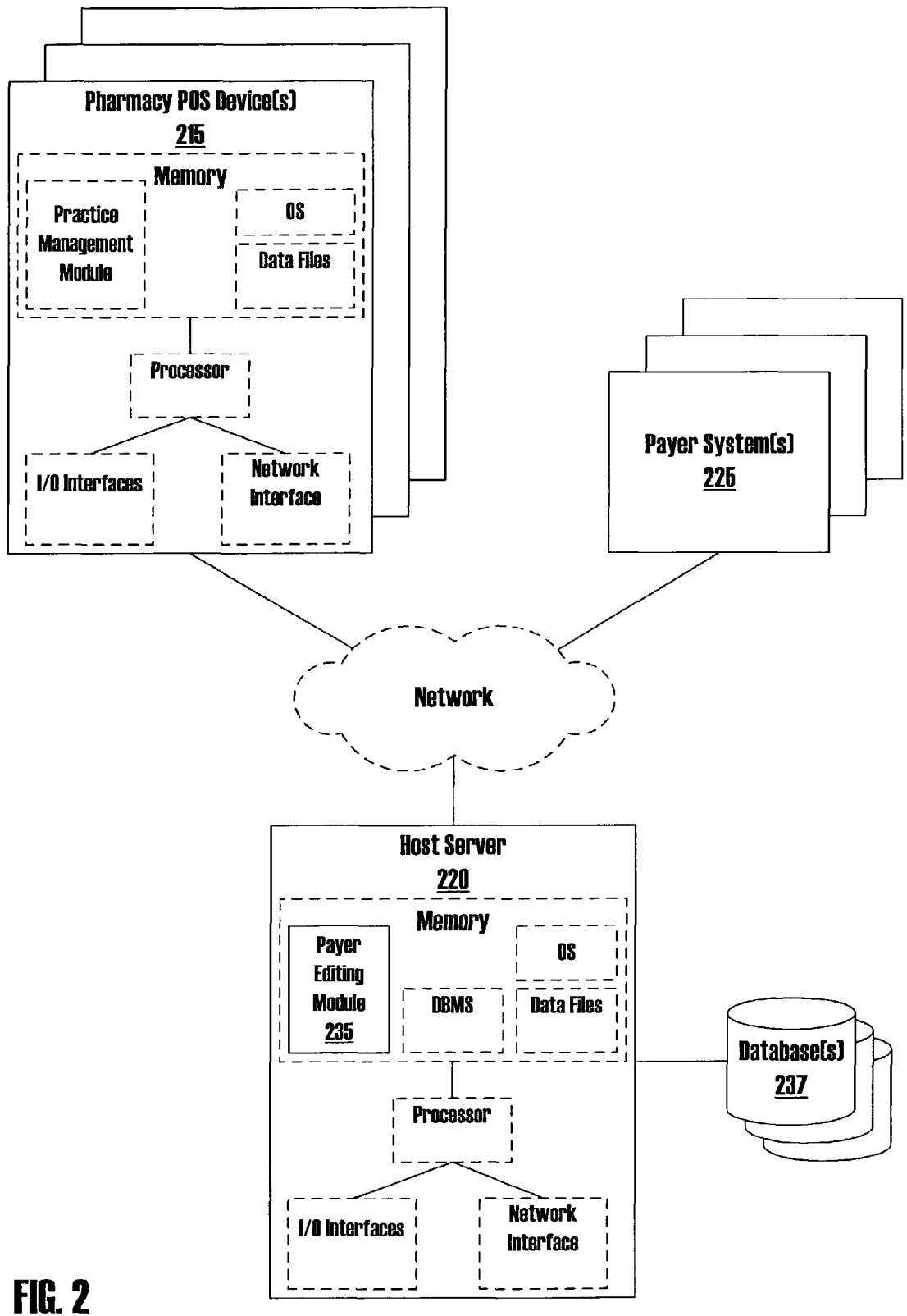
FIG. 2 shows a claim processing system including a payer editing module, according to one aspect of the present invention.

FIG. 2 shows a claim processing system according to a preferred embodiment of the present invention. Like the system of FIG. 1, the system includes a pharmacy POS device 215, a host server 220 and a payer system 225. Similar elements described with respect to FIG. 1 are illustrated in dashed lines and as such, are not further described in FIG. 2. However, unlike the system of FIG. 1, the claim editing module 123 of FIG. 1 is illustrated in FIG. 2 as a payer editing module 235. Although the payer editing module 235 is illustrated and discussed herein as separate from the host server 220, it should be appreciated that the payer editing module 235 can be included in part or in whole within the host server 220 such that some or all of the functions of the payer editing module 235 are internal to the host server 220. Likewise, the host server 220 may include algorithms or hardware and software that work in combination to effect the functions described herein with respect to the payer editing module 235. Briefly, the payer editing module 235 permits the claim processing system of FIG. 2 to review claims according to payer-defined criteria stored in the database(s) 237 to allow the system to identify claims that the payer system 225 would otherwise determine as having some type of problem upon receipt (e.g., the claim is formatted incorrectly or include values that the payer system 225 will not accept).

According to one preferred embodiment of the invention, the payer editing module 235 receives and reviews claims submitted by the provider 215 to the payer system 225 and/or host server 220. The payer editing module 235 is operable to identify those claims that do not meet payer system 225 criteria such that the claims are unacceptable to the payer system 225. Unacceptable claims can comprise claims lacking one or more required fields, claims having too many fields, or claims having data outside pre-established limits defined by the payer, a third party or the host server 220.

In order to identify incomplete or incorrect claim data, the payer editing module 235 preferably identifies, upon receipt of a claim, the intended payer system 225 to which the claim is directed. Additionally, the specific pharmaceutical or medical plan for a particular payer, as identified by the claim, is also determined, as is described in greater detail below. Using this information the payer editing module 235 retrieves the appropriate claim criteria required by the intended recipient payer system 235 for analyzing the claim. This claim criteria may be stored in data files local to the host server 104, or in one or more databases 237 local or remote to the host server 104. Therefore, the payer system 225 provides the payer editing module 235 a detailed list of each claim criteria (or component) the payer system 225 requires such that a claim can be processed and is not considered incomplete. This detailed claim information may be provided by the payer system 225 to the payer editing module 235 via electronic communication, such as via a web page operated by the host sever 220 and providing the payer system 225 a GUI for inputting and/or identifying the claim data the payer system 225 needs to process a claim. This information could also be supplied to the payer editing module 235 via one or more forms received by an administrator or payer editing module 235 data entry person for input into the payer editing module 235. Such forms may be completed by the payer system 225 to identify claim criteria that the payer system 225 wishes the payer editing module 235 to review. The claim criteria may not only indicate the required claim format and claim fields, but also appropriate ranges of data acceptable to the intended recipient payer system 225. Furthermore, as discussed in greater detail below, the claim criteria may indicate parameters permitting the payer editing module 235 to edit the claims as necessary to comply with the payer defined claim criteria. Therefore, the present invention permits parameter-driven claim edits.

As an illustrative an non-limiting example, the claim criteria may require that a checksum digit be included in to the claim contents. Therefore, the payer editing module will compare the claim to the claim criteria, note that the claim does not include a checksum digit, and examine the claim criteria to determine if the payer editing module 235 is permitted to edit the claim by adding the checksum to the claim. Where the claim criteria so permits, the payer editing module will follow the instructions provided by the claim criteria in correcting the claim.

As noted above, it will be appreciated by those of ordinary skill in the art that the payer editing module 235 comprises at least one database, e.g., database 237, for storing the requisite claim criteria required to process claims for payer systems 225 that wish to receive claims verified using the system. Because each payer system 225 may require different criteria to process claims, separate claim criteria files may be maintained and accessed by the payer editing module 235 for each payer, where the payer editing module 235 first identifies the payer system 225 to which a claim generated by a provider 215 is intended, and thereafter compares the claim data to the criteria for the identified payer system 225.

The payer system 225 may be identified in the claim data or by data accompanying the claim data. For instance, where the communication is electronic using Internet Protocol, one or packets comprising a header may reveal the identity of the intended payer system 225 to which the claim data is intended to be received. This information is intercepted by the host server 220, which identifies the pharmacy POS device 215 and the payer system 225. The host server 220 may examine the provider (i.e., the transmitting pharmacy) identity to determine whether the provider's claims should be examined by the payer editing module 235 and if so, the claim criteria the that should be used to examine the submitted claim data. For example, although multiple providers 215 may utilize the host server 220 (e.g., for the services identified above, including its function as a network provider), some of the providers 215 may elect not to use the payer editing module 235 described herein. Therefore, the host server 220 can identify the origin of the provider and intercept for screening by the payer editing module 235 only those claims associated with providers that wish to use, or pay for, the payer editing module 235. According to another aspect of the invention, the identity of the payer system 225 may also be used to determine whether a claim is reviewed by the payer editing module 235.

After claims are compared to the payer-identified claim criteria, a comprehensive report may be created at the end of transmission which indicates whether it has passed the payer editing module 235 and if the claim will be forwarded to the intended payer system 225. The payer editing module 235 thus performs real-time validation and data management of pharmacy claim submission data to maximize claim reimbursement and minimize claim submission errors. The present invention provides unparalleled flexibility, allowing for parameter-driven edits, including editing actions, messages and thresholds based on provider business requirements.

Figure 3:
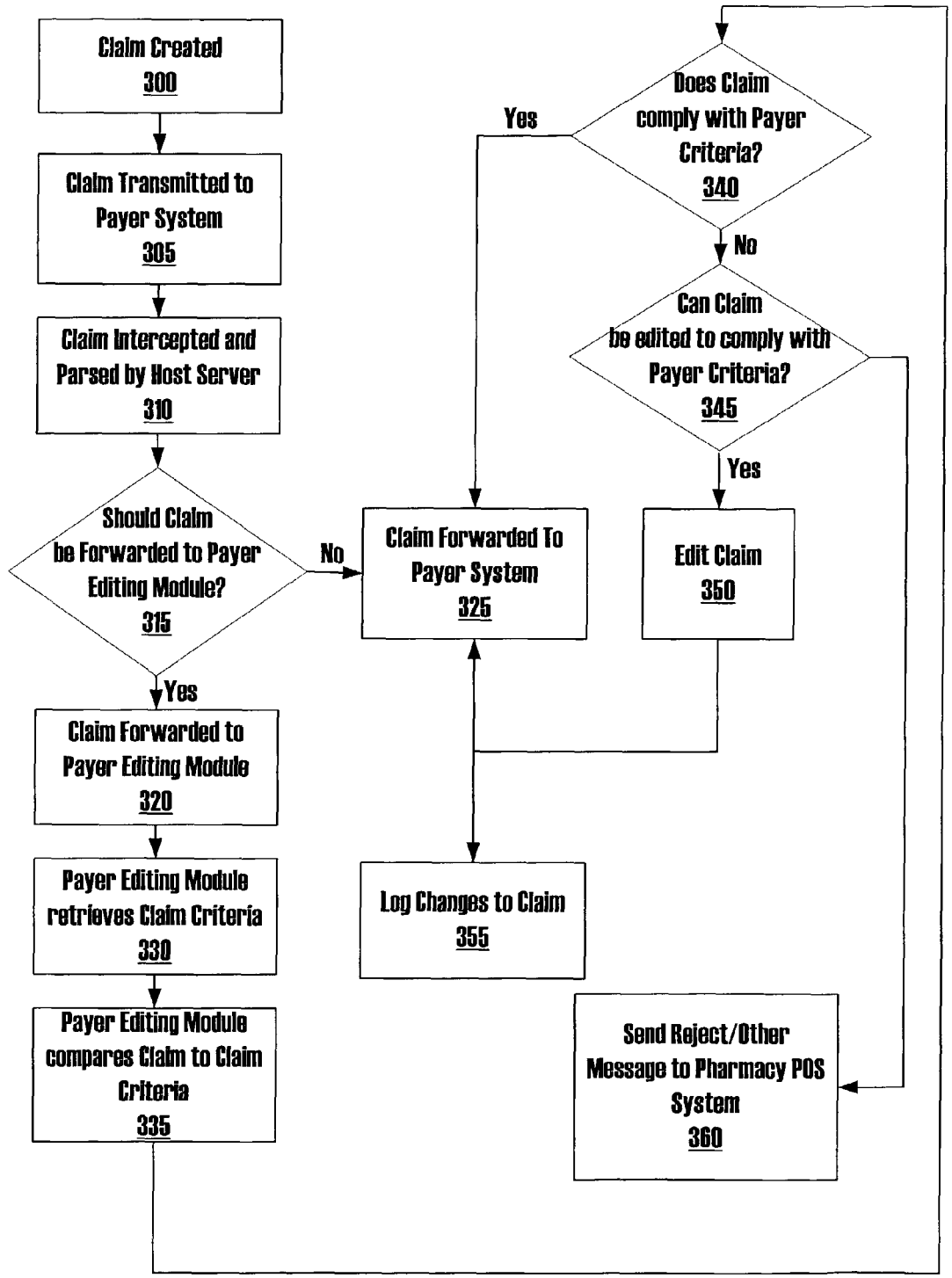
FIG. 3 shows a block diagram flowchart showing a payer editing process according to one embodiment of the present invention.

The present invention will be better understood with reference to an illustrative example, the basic process of which is illustrated in the block diagram flow chart of FIG. 3. Upon creating a claim (block 300), a pharmacy POS device 215 submits a claim, e.g., corresponding to a pharmaceutical prescription, to the payer system 225 (block 305). The host server 220 then intercepts and parses the claim to identify the intended payer system (block 310), and determines if the payer system 225 is a pharmacy that has subscribed to the payer editing module 245 (block 315). If so, the host server 220 forwards the claim to the payer editing module 245 (block 320). Otherwise, the claim is passed to the payer system without further screening (block 325). When the payer editing receives the claim, the payer editing module 235 retrieves the appropriate payer claim criteria (block 330) for evaluating the claim and then compares the claim to the payer claim criteria (block 335) to determine if the claim contains the appropriate content, including whether the claim is in a format supported by the intended payer, if the claim contains the appropriate fields, if the claim fields include correct data defined by the payer or a third party, and/or if the claim contents fall within threshold values provided by the payer or based on third party information. As an illustrative example, a payer may have established claim criteria requiring that a person code within a pharmaceutical claim must have a value of "01" or higher. If a claim, submitted in the syntactical format as dictated by the payer, contains a person code with a value of "00", implementation instructions provided by the payer editing system will analyze the claim, determine that only person codes of "01" and greater should be accepted, and the claim is rejected back to the pharmacy with an appropriate rejection code (e.g., "Person Code Rejection") to allow the claim to be resubmitted with the correct information.

If the claim complies with the payer claim criteria (block 340) the payer editing module 235 will forward the claim to the payer (block 325). Alternatively, the payer editing module 235 may identify that the pharmacy claim does not meet the payer claim criteria (block 340). As another example, the claim may not meet a payer protocol that is required for the payer system 225 to process the electronic claim. As described above, the payer editing module 245 can make this determination based upon a comparison of the claim data (e.g., the claim protocol) with claim criteria (e.g., required claim protocol) provided by the payer system 225. The payer editing module 245 can then edit the claim (block 350), if possible and/or instructed to do so by the payer provided criteria (block 345), to conform to the payer criteria, or alternatively, the payer editing module can identify the problem and return the claim to the provider with an error or reject message identifying the problem (block 360) so that the provider can take the necessary steps to correct the claim. If the payer editing module 245 edits the claim (block 350) to conform to the payer criteria as instructed by the claim criteria provided by the payer, the claim may then be transmitted to the payer system (block 325), and the changes to the claim are logged (block 355) such that the changes can be viewed by the payer or pharmacy at a later time via a payer edit interface (not illustrated) of said host server. The payer edit interface may be accessible by the payer system via the Internet such that any and all claim edits made be viewed via a graphical user interface.

Because the payer-provided claim criteria is highly customizable on a payer-by-payer basis, the system maximizes claim reimbursement and minimizes errors through customizable financial and validation edits. Therefore, providers can ensure appropriate reimbursement for pharmacy claims and optimize their market share and rebate program participation. Additionally, because the system provides real-time messaging alerts or retrospective reports supporting Usual & Customary price comparisons, AWP edits, DAW brand appropriateness, and numerous other edits, payer profitability can be maximized. Additionally, by reducing potential claim submission errors at the point of sale, the provider can receive maximum reimbursement value without allocating unnecessary time and resources retrospectively.

Non-limiting examples of the types of screening edits that may be executed by the payer editing module 235 at the payers' request include those listed in Table 1, below:

TABLE 1

Example Payer Edits

| Edit Name | Description |
| --- | --- |
| AWP Validation Edit | Edit may validate the submitting cost against an outside cost database, e.g., within database 237. |
| Companion Product Messaging Edit | This edit may be invoked where a selected medication matches a companion OTC product, as identified in a database of OTC products (stored within database 237). Recommendations for the OTC product may be kicked back to the pharmacy prior to the claim being processed. |
| DEA Edit | Validates the presence and format of the submitted physician DEA number. Compares DEA number to the federal NTIS file, updated monthly. |
| Diagnosis Code Edit | Edit ensures an entry in the "Diagnosis Code" field included within a claim. |
| Duplicate Claim Edit | May be used to determine if a payer receives multiple submissions for a claim for the same Cardholder, Medication, and Date of Service within a defined period of time in which the claim has previously been paid. Returns a rejection response to pharmacy requiring pharmacy interaction. |
| Expected Reimbursement Edit | Edit identifies variances in claim reimbursement by comparing third party plan payment against the ingredient cost and dispensing fee submitted. |
| Look alike, sound alike | Used to verify that an error has not been made in the dispensing of the product |
| Typical Dosing | Used to verify that the prescription, as filled, provides the appropriate dosing for the patient, given age and gender |

Figure 4:
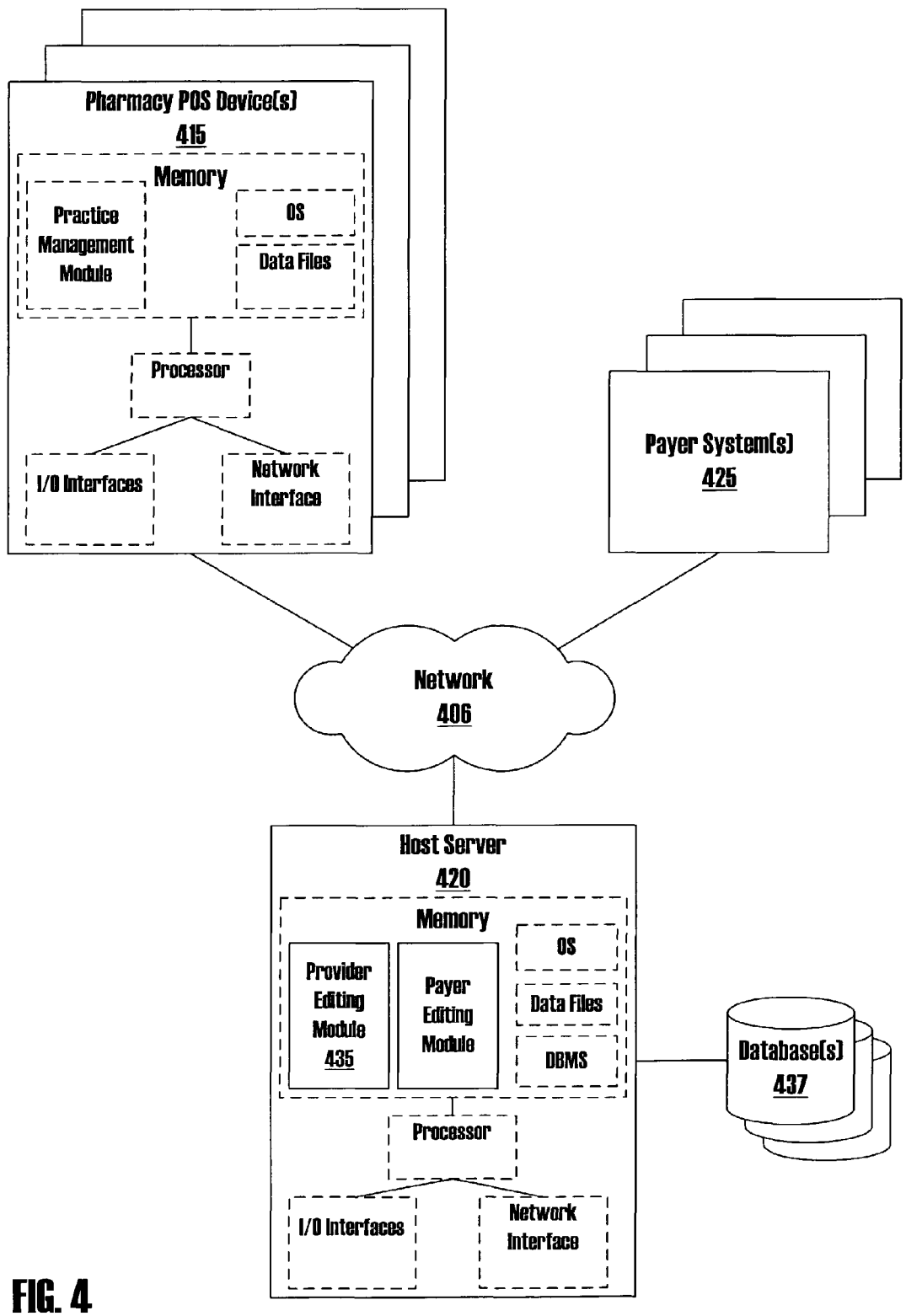
FIG. 4 shows a claim processing system including a provider editing module and a payer editing module, according to one aspect of the present invention.

Next, FIG. 4 shows a host server including both a provider editing system and a payer editing module, according to one aspect of the present invention. Therefore, the system 450 illustrated in FIG. 4 combines the functionality described above with respect to FIGS. 2 and 3 with provider-submitted claim criteria. As a result, both providers 415 and payers 425 can identify claim errors rapidly to minimize delay and unnecessary expenses in processing claims.

The system of FIG. 4 is identical to the system of FIG. 2 but for the addition of a provider editing module 435. Thus, in addition to the payer editing process described above with respect to FIGS. 2 and 3, the claims undergo a provider-based claim screening and edit process. Like the systems of FIGS. 1 and 2, the system includes a pharmacy POS device 415, host server 420 and payer system 425 in communication via a network 406. Although the provider editing module 435 is illustrated and discussed herein as separate from the host server 420, it should be appreciated that the provider editing module 435 can be included in part or in whole within the host server 420 such that some or all of the functions of the provider editing module 435 are internal to the host server 420. Likewise, as described above with respect to FIG. 1, the host server 420 may include algorithms or hardware and software that work in combination to effect the functions described herein with respect to the provider editing module 435.

According to one preferred embodiment of the invention, the provider editing module 435 receives and reviews claims submitted by the pharmacy POS device 415 to the payer system 425 and/or host server 420. The provider editing module 435 is operable to identify those claims that do not meet provider-established criteria such that the claims are in a form that the provider (e.g., pharmacy) deems undesirable. Unacceptable claims can comprise claims having data outside pre-established limits defined by the provider, a third party or the host server 420.

In order to identify incomplete or incorrect claim data, the provider editing module 235 may identify, for each provider, the claim criteria required by the provider. Therefore, the provider may provide the provider editing module 435 a detailed list of each claim criteria (or component) the provider requires such that a claim can be processed and is not considered incomplete. It will be appreciated by those of ordinary skill in the art that the provider editing module 435 is in communication with at least one database 437 for storing the requisite provider claim data required to process claims for providers that wish to utilize the provider editing module 435. Because each provider may require different criteria to process claims, separate claim criteria files may be maintained and accessed by the provider editing module for each provider, where the provider editing module 435 first identifies the provider which generates a claim, and thereafter compares the claim data to the provider-identified or third party criteria. Alternatively, the provider editing module 435 can independently review the claims to ensure that no fields are blank or empty; in such a scenario the provider editing module 435 need not receive any information from the pharmacy POS system 415 other than the claim data.

The function of the system illustrated in FIG. 2 will be better understood with reference to the following example. For instance, a pharmacy may submit a claim corresponding to a pharmaceutical prescription to the host server 420. The host server 420 identifies that the provider is a pharmacy that has subscribed to the provider editing module 435, and as such, forwards the claim to the provider editing module 435. The provider editing module 435 examines the claim to determine if the claim contains the appropriate data, including whether the appropriate fields contain data and whether the data within those fields is within a correct threshold. For example, the provider editing module 435 may identify that the pharmacy should be requesting a $20 reimbursement from a payer system 425 instead of a $10 reimbursement requested in the electronic claim. The provider editing module 435 can make this determination based upon a comparison of the claim data with criteria provided by the payer system 425, information provided by the host server 420, or information provided by a third party (e.g., a drug database) in communication with the host server 420. Accordingly, the provider editing module 435 can change the reimbursement request to $20 and forward the claim to the appropriate payer system 425. Alternatively, where a claim is incomplete or lacks a field that is unknown to the provider editing module 435, the provider editing module 435 can identify the problem and return the claim to the provider 415 with a rejection message or an error identifying the problem so that the provider can take the necessary steps to correct the claim. Continuing with the example, where the payer system 425 approves the claim, the transaction proceeds back though the provider editing module 435 so that the provider editing module 435 can maintain an appropriate record of the transaction (e.g., that the provider editing module 435 saved the provider $10 on a claim accepted by the payer system 425).

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for providing real time or near real time editing of prescription claim content prior to adjudication of a prescription claim, comprising:

storing a plurality of pre-established prescription claim criteria associated with a payer system in memory, wherein the plurality of pre-established prescription claim criteria includes criteria previously submitted by the payer system to a host server computer system;

receiving, at the host server computer system, a prescription claim from a pharmacy point-of-service (POS) device, wherein the prescription claim includes a plurality of prescription claim contents and wherein a portion of the prescription claim contents indicates that the prescription claim is directed to the payer;

accessing, from the memory, the plurality of pre-established prescription claim criteria associated with the payer system;

comparing, by the host server computer system, at least one of plurality of prescription claim contents to the plurality of pre-established prescription claim criteria associated with the payer system;

determining, based on the comparison of at least one of the plurality of prescription claim contents to the plurality of pre-established prescription claim criteria associated with the payer system, that at least one of plurality of prescription claim contents should be compared to objective information accessible by the host server computer system and provided by at least one party other than the pharmacy associated with the pharmacy POS device or the payer;

comparing, by the host server computer system, at least one of the plurality of prescription claim contents to the objective information;

editing, by the host server computer system, at least one of the plurality of prescription claim contents in the prescription claim based on the comparison of at least one of the plurality of prescription claim contents to the objective information, wherein the editing modifies at least one of the plurality of prescription claim contents creating an edited prescription claim; and transmitting the edited prescription claim to the payer for subsequent adjudication.

2. The method of claim 1, further comprising forwarding a message to the pharmacy POS device, wherein the message includes an indication that the prescription claim did not contain the correct prescription claim contents.

3. The method of claim 1, wherein the objective information includes historical consumer claim information.

4. The method of claim 1, wherein the host server computer system is in electrical communication with the payer system via the Internet.

5. The method of claim 1, further comprising storing at least one of the plurality of prescription claim contents prior to the editing.

6. The method of claim 1, further comprising storing at least one of the edited prescription claim contents after the editing.

7. The method of claim 1, wherein the prescription claim includes data associated with filling a prescription or requesting approval for payment from the payer system.

8. The method of claim 1, wherein editing at least one of the plurality of prescription claim contents in the prescription claim based on the comparison of at least one of the plurality of prescription claim contents to the objective information includes adding additional prescription claim content to the prescription claim.

9. The method claim 1, wherein the plurality of pre-established prescription claim criteria comprises at least one of physician information, payer information, drug information, drug price information, or drug dosage information.

10. The method of claim 1, further comprising:
prior to transmitting the edited prescription claim to the payer for subsequent adjudication:
accessing, from the memory, a plurality of pre-established prescription claim criteria associated with the pharmacy provider;
comparing, by the host server computer system, at least one of plurality of prescription claim contents to the plurality of pre-established prescription claim criteria associated with the pharmacy provider; and
editing at least one of the plurality of prescription claim contents in the prescription claim based on the comparison of at least one of the plurality of prescription claim contents to the plurality of pre-established prescription claim criteria associated with the pharmacy provider.

11. A system for providing real time or near real time editing of prescription claim content prior to adjudication of a prescription claim, comprising:
at least one database, wherein the at least one database stores a plurality of pre-established prescription claim criteria associated with a payer system in the at least one database;
a host server computer system in communication with the at least one database, wherein the plurality of pre-established prescription claim criteria includes criteria previously submitted by the payer system to the host server computer system, and wherein the host server computer system is configured to execute instructions to:

receive a prescription claim from a pharmacy point-of-service (POS) device, wherein the prescription claim includes a plurality of prescription claim contents and wherein a portion of the prescription claim contents indicates that the prescription claim is directed to the payer;

access, from the at least one database, the plurality of pre-established prescription claim criteria associated with the payer system;

compare at least one of plurality of prescription claim contents to the plurality of pre-established prescription claim criteria associated with the payer system;

determine, based on the comparison of at least one of the plurality of prescription claim contents to the plurality of pre-established prescription claim criteria associated with the payer system, that at least one of plurality of prescription claim contents should be compared to objective information accessible by the host server computer system and provided by at least one party other than the pharmacy associated with the pharmacy POS;

compare at least one of the plurality of prescription claim contents to the objective information;

edit at least one of the plurality of prescription claim contents in the prescription claim based on the comparison of at least one of the plurality of prescription claim contents to the objective information, wherein the editing modifies at least one of the plurality of prescription claim contents creating an edited prescription claim; and transmit the edited prescription claim to the payer for subsequent adjudication.

12. The system of claim 11, wherein the host server computer system is further configured to execute instructions to forward a message to the pharmacy POS device, wherein the message includes an indication that the prescription claim did not contain the correct prescription claim contents.

13. The system of claim 11, wherein the objective information includes historical consumer claim information.

14. The system of claim 11, wherein the host server computer system is in electrical communication with the payer system via the Internet.

15. The system of claim 11, wherein the host server computer system is further configured to execute instructions to store at least one of the plurality of prescription claim contents prior to the editing.

16. The system of claim 11, wherein the host server computer system is further configured to execute instructions to store at least one of the edited prescription claim contents after the editing.

17. The system of claim 11, wherein the prescription claim includes data associated with filling a prescription or requesting approval for payment from the payer system.

18. The system of claim 11, wherein the instructions to edit at least one of the plurality of prescription claim contents in said prescription claim based on the comparison of at least one of the plurality of prescription claim contents to the objective information include instructions to add additional prescription claim content to the prescription claim.

19. The system claim 11, wherein the plurality of pre-established prescription claim criteria includes at least one of physician information, payer information, drug information, drug price information, or drug dosage information.

20. The system of claim 11, wherein the host server computer system is further configured to execute instructions to:
prior to transmitting the edited prescription claim to the payer for subsequent adjudication:
- access, from the at least one database, a plurality of pre-established prescription claim criteria associated with the pharmacy provider;
- compare at least one of plurality of prescription claim contents to the plurality of pre-established prescription claim criteria associated with the pharmacy provider; and
- edit at least one of the plurality of prescription claim contents in said prescription claim based on the comparison of at least one of the plurality of prescription claim contents to the plurality of pre-established prescription claim criteria associated with the pharmacy provider.

* * * * *

UNITED STATES PATENT AND TRADEMARK OFFICE
CERTIFICATE OF CORRECTION

PATENT NO.       : 8,190,453 B2                              Page 1 of 1
APPLICATION NO.  : 10/439422
DATED            : May 29, 2012
INVENTOR(S)      : James Couser Rowe, III et al.

It is certified that error appears in the above-identified patent and that said Letters Patent is hereby corrected as shown below:

In the Claims

Column 12, line 64, of claim 1 after "device or the payer" insert --, wherein objective information comprises one or more of drug lists, physician DEA (Drug Enforcement Agency) numbers, or historical consumer claim information--.

Column 14, line 22, of claim 11 after "macy POS" insert --device or the payer, wherein objective information comprises one or more of drug lists, physician DEA (Drug Enforcement Agency) numbers, or historical consumer claim information--.

Signed and Sealed this
Twenty-third Day of September, 2014

Michelle K. Lee
*Deputy Director of the United States Patent and Trademark Office*